US012611529B2

(12) United States Patent
Krespi et al.

(10) Patent No.: US 12,611,529 B2
(45) Date of Patent: Apr. 28, 2026

(54) DELIVERY DEVICE FOR EUSTACHIAN TUBE PROCEDURES

(71) Applicant: Valam Corporation, Ridgefield, CT (US)

(72) Inventors: Yosef Krespi, Ridgefield, CT (US); Ron Hadani, Even-Yahuda (IL)

( * ) Notice: Subject to any disclaimer, the term of this patent is extended or adjusted under 35 U.S.C. 154(b) by 950 days.

(21) Appl. No.: 17/843,840

(22) Filed: Jun. 17, 2022

(65) Prior Publication Data

US 2022/0401713 A1 Dec. 22, 2022

Related U.S. Application Data

(60) Provisional application No. 63/225,934, filed on Jul. 26, 2021, provisional application No. 63/212,115, filed on Jun. 18, 2021.

(51) Int. Cl.
*A61M 29/02* (2006.01)

(52) U.S. Cl.
CPC ....... *A61M 29/02* (2013.01); *A61M 2029/025* (2013.01); *A61M 2210/0675* (2013.01)

(58) Field of Classification Search
CPC ............ A61M 29/02; A61M 2029/025; A61M 2210/0675; A61M 2210/0662; A61M 2210/0668; A61M 25/00; A61M 29/00
See application file for complete search history.

(56) References Cited

U.S. PATENT DOCUMENTS

| | | | | |
|---|---|---|---|---|
| 1,636,969 | A | * | 7/1927 | Rose ................... A61M 3/0291 604/107 |
| 5,893,828 | A | * | 4/1999 | Uram ..................... A61B 90/37 606/15 |
| 6,425,853 | B1 | | 7/2002 | Edwards |
| 6,692,490 | B1 | | 2/2004 | Edwards |

(Continued)

FOREIGN PATENT DOCUMENTS

| | | | |
|---|---|---|---|
| AU | 2012202103 | B2 | 3/2012 |
| EP | 1281366 | B1 | 10/2006 |

(Continued)

OTHER PUBLICATIONS

European Patent Office Search Report Listing Search References (Sep. 29, 2023) for European Patent Application 23179641.8.

(Continued)

*Primary Examiner* — Rebecca E Eisenberg
(74) *Attorney, Agent, or Firm* — Joseph P. Aiena

(57) ABSTRACT

There is provided a device for eustachian tube treatments having a handle section with proximal and distal ends where the handle section has a dilator control with at least first and second positions. The dilator control is connected to a plate internal to the handle section, which is connected to an internal shaft. An insertion tube is connected to the plate and extends from the distal end of the handle section. A protective sleeve is inside of the insertion tube and connected to the plate. A dilator is connected at a first end to the plate and collapsed within the protective sleeve, with the dilator (Continued)

expanding when moved to a position external to the distal end of the insertion tube and the protective sleeve is withdrawn back into the insertion tube. The dilator maintains the eustachian tube open for delivery of laser energy or therapeutics to a desired treatment area.

13 Claims, 16 Drawing Sheets

(56)                References Cited

U.S. PATENT DOCUMENTS

| | | | |
|---|---|---|---|
| 7,326,235 | B2 | 2/2008 | Edwards |
| 8,282,667 | B2 * | 10/2012 | Drontle ................. A61M 25/10 |
| | | | 606/196 |
| 10,786,653 | B2 * | 9/2020 | Galgano ............... A61M 25/09 |
| 11,020,571 | B2 * | 6/2021 | Belson ............. A61M 25/0631 |
| 2006/0147492 | A1 | 7/2006 | Hunter et al. |
| 2007/0156225 | A1 * | 7/2007 | George ..................... A61F 2/95 |
| | | | 606/108 |
| 2010/0087798 | A1 | 4/2010 | Adams et al. |
| 2010/0198191 | A1 | 8/2010 | Clifford et al. |
| 2010/0274188 | A1 | 10/2010 | Chang et al. |
| 2016/0008017 | A1 | 1/2016 | Makower et al. |
| 2016/0287065 | A1 * | 10/2016 | Ha ..................... A61B 1/00154 |
| 2018/0280046 | A1 | 10/2018 | Ngo-Chu et al. |
| 2019/0175413 | A1 | 6/2019 | Campbell et al. |
| 2020/0100896 | A1 | 4/2020 | Jimenez et al. |
| 2020/0187967 | A1 * | 6/2020 | Palushi ............. A61M 25/1018 |
| 2021/0007762 | A1 | 1/2021 | Chang et al. |
| 2024/0382724 | A1 * | 11/2024 | Chu ..................... A61M 29/02 |

FOREIGN PATENT DOCUMENTS

| | | | |
|---|---|---|---|
| IN | 5650DELNP2012 | A | 7/2014 |
| WO | WO2005117755 | A2 | 12/2005 |
| WO | WO2011082139 | A1 | 7/2011 |
| WO | WO2016160967 | | 10/2016 |

OTHER PUBLICATIONS

European Patent Office Search Report for European Patent Application 23179641.8, citing Jimenez et al. (US 2020/100896A1), Sep. 29, 2023.

* cited by examiner

DELIVERY DEVICE FOR EUSTACHIAN TUBE PROCEDURES

CROSS REFERENCE TO RELATED APPLICATIONS

This application claims benefit of and priority to U.S. Provisional Application Ser. No. 63/212,115 filed on Jun. 18, 2021 and U.S. Provisional Application Ser. No. 63/225,934 filed on Jul. 26, 2021, each of which are incorporated herein by reference in their entirety.

FIELD OF THE INVENTION

This invention relates to the field of delivery systems for entry or access ports usable in medical procedures, more particularly delivery systems and methods for nasal access ports.

BACKGROUND

The nasal cavity is a hollow space within the nose and skull that is lined with hair-bearing skin and mucus membrane. The function of the nasal cavity is to warm, moisturize, and filter air entering the body before it reaches the lungs. Hairs and mucus lining the nasal cavity help to trap dust, mold, pollen, microbes, and other environmental contaminants before they can reach the trachea and the lungs.

The nasal septum separates the nasal cavity into two, substantially symmetrical spaces and is made up of the perpendicular plate of the ethmoid bone, the vomer and the septal cartilage. Superiorly, the nasal cavity is limited by several bones including the nasal bone, the frontal bone, the cribriform plate of the ethmoid bone and the body of the sphenoid bone. Anteriorly, the outer nose including the nasal bones and the attached cartilage and skin can be seen, with the two nostrils creating constant communication with the external environment. Inferiorly, the palatine process of the maxilla and the horizontal plate of the maxilla form a solid base lined with respiratory epithelium. Posteriorly, the choanae of the skull are situated. Laterally as with superiorly, a range of cranial bones surround the cavity including the maxilla, the ethmoid bone, the palatine bone, the sphenoid bone, the inferior nasal concha and the lacrimal bone. The nasal-sinus cavity and the middle ear are connected by the eustachian tube. The functions of the eustachian tube are to drain fluid from the middle ear, maintain pressure balance in the middle ear, and insulate the ear from sounds of the body. Pain and pressure are experienced in the ear when there is fluid buildup due to the eustachian tube not opening properly or sufficiently. Common eustachian tube disorders include patulous eustachian tube dysfunction, obstructive eustachian tube dysfunction, and baro-challenge induced eustachian tube dysfunction (such as pressure felt in the ears with airplane travel).

SUMMARY OF THE INVENTION

The present invention provides a therapeutic solution for Eustachian Tube Dysfunction (ETD) conditions such as when the eustachian tube remains closed or remains open all the time. The device and method of the present invention keeps the eustachian tube open during procedures. As the eustachian tube is a generally flat or closed structure, there is a need to dilate and keep the eustachian tube open and expend its mucosa folds during the procedure to be exposed to the delivery of therapeutic means such as laser energy or drugs. The present invention is useful for all dysfunction conditions of ETD, including for a closed eustachian tube and also for a patulous eustachian tube condition.

The steps in the method are as follows: first, the indicated device of the present invention is inserted trans-nasally until the distal tip of the indicated device reaches the opening of the eustachian tube. Then a dilating element which is kept closed by and within a protective sleeve is inserted and intubates the eustachian tube. During the insertion of the dilating element into the eustachian tube, the protective sleeve encapsulates and keeps the dilating element closed, and prevents any direct contact between the dilating element and the eustachian tube mucosa walls to avoid injury of the mucosa. The dilating element and the protective sleeve are inserted until the distal tip of the dilating element, which extends beyond the protective sleeve reaches the isthmus. Then the protective sleeve is pulled backward into the insertion tube of the indicated device, to expose the dilating element and allow it to open and dilate and expand the eustachian tube walls as indicated with the device of the present invention. Then, the method inserts a therapeutic means through the device to its distal end and through the openings of the dilating element to the eustachian tube's exposed and expended mucosa folds. The therapeutic means that may be inserted and delivered through the device may include drugs, surfactant, saline, or other means such as laser fiber diffuser. The device allows for the delivery of one or multiple therapeutic means at the same time, for example delivery of a substance that is activated by certain wavelength illumination, ultrasound, temperature or temperature change. For example, in the case of delivering laser energy via a laser fiber diffuser, the laser is activated upon the laser fiber diffuser reaching the distal tip of the dilating element. After being deactivated the laser fiber diffuser is removed from the device. Then, the protective sleeve is pushed forward over the dilating element. The protective sleeve collapses and closes the dilating element and covers it. Then, the protective sleeve and the dilating element inside it, are pulled out from the eustachian tube, while the protective sleeve prevents any contact between the dilating element and the eustachian tube's mucosa wall to avoid possible irritation or injury. When the distal ends of the dilating element and its protective sleeve reach the distal tip of the insertion tube of the device, the device is removed from the patient's nose.

A complete eustachian tube treatment is provided. The present invention allows for anatomically precise, atraumatic dilation and a proprietary laser fiber illumination with anti-inflammatory properties. The present invention provides directly targeted drug delivery to the eustachian tube wall—(i.e., steroid, antibiotics, antimicrobial-off label) or surfactant. The present invention provides direct washing of the eustachian tube (i.e., saline) and suction. Laser tuboplasty means for patulous eustachian tube is included with the present invention, as is tuboplasty means in general.

The present invention provides a device for eustachian tube procedures which comprises a handle piece and an insertion tube with a dilating element having an open structure such as a stent-like or a basket shape contained in a protective sleeve within the insertion tube when the dilating element and the protective sleeve are in a first position (flush with the distal end of the insertion tube of the device). The distal end of the dilating element comprises an atraumatic section, including a dome-shaped tip. The dilating element inside the protective sleeve are extended and pushed outward of the insertion tube of the device to a second position. Then the dilating element expands when the protective sleeve is retracted back to the first position by operation of the handle piece. With the device of the present invention, at least one camera is mounted onto the insertion tube of the device to provide visibility during a medical procedure. The device of the present invention may include at least one camera to provide visibility during a medical procedure. The cameras may include a forward looking camera and a backward looking camera to assist in the procedures.

The present invention includes a device for eustachian tube treatments where the device has a handle section having a proximal end and a distal end and the handle section has a dilator control on the outer surface of the handle section, with the dilator control having at least a first position and a second position. The dilator control is connected to a plate internal to the handle section and the plate is connected to an internal shaft. A pin is connected to the plate and contacting a latch for engagement to slide forward and backward the protective sleeve. An insertion tube is connected to the plate and extending from the distal end of the handle section, with the insertion tube having an opening at a distal end of the insertion tube. A protective sleeve is inside of the insertion tube and connected at a first proximal end of the protective sleeve to the plate, along with a dilating element connected at a first proximal end of the dilating element to the plate and collapsed within the protective sleeve. The dilating element is capable of expanding when moved to a position external to the distal end of the insertion tube and the protective sleeve is withdrawn back into the insertion tube. The device of the present invention includes where the dilator control is moved to the second position to move the plate and the internal shaft forward and thereby move the dilating element and the protective sleeve to the position external to the distal end of the insertion tube.

In an embodiment, the device of the present invention includes where the pin activates the latch, so that the protective sleeve can slide off or back on the dilating element. In an embodiment, the device of the present invention includes where the dilating element comprises multiple struts, ribs or blades which expand into an open shape when the protective sleeve is withdrawn from the dilating element. In an embodiment, the device of the present invention includes where the dilating element is a cross hatched mesh shape which expands when the protective sleeve is withdrawn off it. In any shape, the dilator forms a basket with open walls when expanded which support and push radially (or sideway) open the surrounding tissue. The device of the present invention therefore allows for therapeutic treatment by allowing direct delivery of different substances (i.e., surfactant, steroids, antibiotics, etc.), ultrasound, light or laser energy to be delivered through the openings between the wires of the frame of the dilating element. In an embodiment, the device according to the present invention includes where the dilating element has an atraumatic distal section and tip.

The device of the present invention includes where the handle section has an opening port at the proximal end to receive a syringe or other means of delivering drugs or inserting a laser fiber, or to provide suction capability. In an embodiment, the device of the present invention further includes a camera control knob positioned on the insertion tube external to the handle section. In an embodiment, the device of the present invention further includes a connecting tube connecting with and extending from the camera control knob to connect to a camera housing, and the camera housing can include a video camera with illumination means.

The present invention includes processes for using the device described herein for treatment of eustachian tube dysfunction.

BRIEF DESCRIPTION OF THE DRAWINGS

Exemplary embodiments are illustrated in referenced figures. Dimensions of components and features shown in the figures are generally chosen for convenience and clarity of presentation and are not necessarily shown to scale. The figures are listed below where.

DETAILED DESCRIPTION

The present invention is a eustachian tube therapeutic delivery device with an optional integrated camera. The device is to treat eustachian tube dysfunction, by inserting a collapsed, closed, small diameter dilator into the eustachian tube. The dilator is designed such that when it is expanded, most of the surrounding tissues are exposed and are not in contact with its structure. This allows for delivery of therapeutic substances from the proximal end of the device to reach the inside of the eustachian tube and to come in direct contact with the mucosa without the dilator being a barrier in between, as in the case of a balloon dilator. The opened structure of the dilating element further allows for suction of secretion and mucus from the eustachian tube, which is also not possible with balloon dilators. The expansion of the dilator and the change of its shape occurs either by its own mechanical shape and material memory (such as nitinol), or by applying force to change and expend the dilator shape.

The dilating basket in the exposed, expanded position will open the eustachian tube by the wires pushing outward and can maintain the eustachian tube folds in an open state for the medical procedure and allow for therapeutic delivery (i.e., drugs, laser energy etc.) directly to the desired exposed tissue area. It is noted that other shapes for the dilating element are within the scope of the present invention, such as various mesh stent-like shapes, spirals or prongs. As long as the shapes are able to push out and maintain the eustachian tube in open position.

Figure 1:
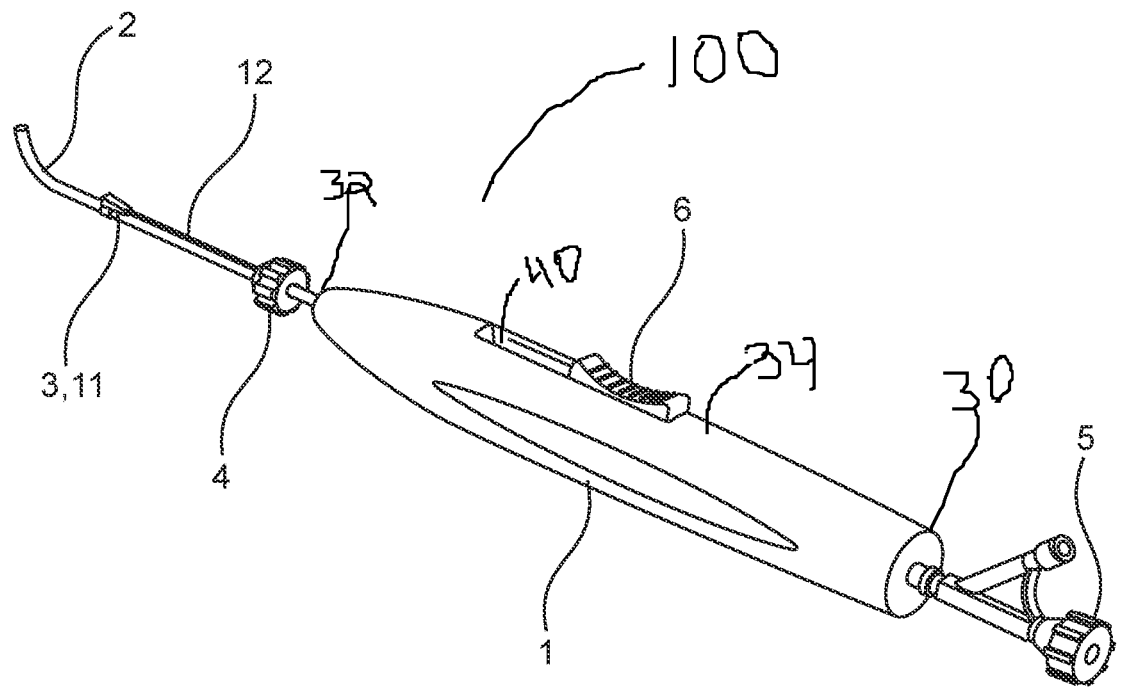
FIG. 1 is an illustration of the device of the present invention.

Referring to FIG. 1, there is shown the device 100 of the present invention. The device 100 includes a rigidly formed, cylindrically shaped main handle section 1, with a handle proximal end 30 and a handle distal end 32, with a dilator control slider 6 within slot 40 on an outer surface 34 as a part of the cylindrical handle section 1. At the handle proximal end 30, there is an opening to receive and attach a port for connection, such as a luer type port, which can be a single port or with bifurcation as shown in the illustration of FIG. 1. Extending from the handle distal end 32 is a thinner, rigid needlelike insertion tube 2 with an opening 36 at the distal end 38 of the insertion tube, from which the protective sleeve 7 and dilator 8 will be pushed out of when the device 100 is in use by a medical professional as more fully described herein, Positioned on the insertion tube 2 and external to the main handle 1 is a camera control knob 4. A connecting tube 12 connects with and extends from the camera control knob 4 to contain the camera's electronic cable (not shown) and connect with a camera housing 3 and an optionally included video camera 11, both of which are positioned on the insertion tube 2 at a location closer to distal end 38 of insertion tube 2 than camera control knob 4.

Figure 2A:
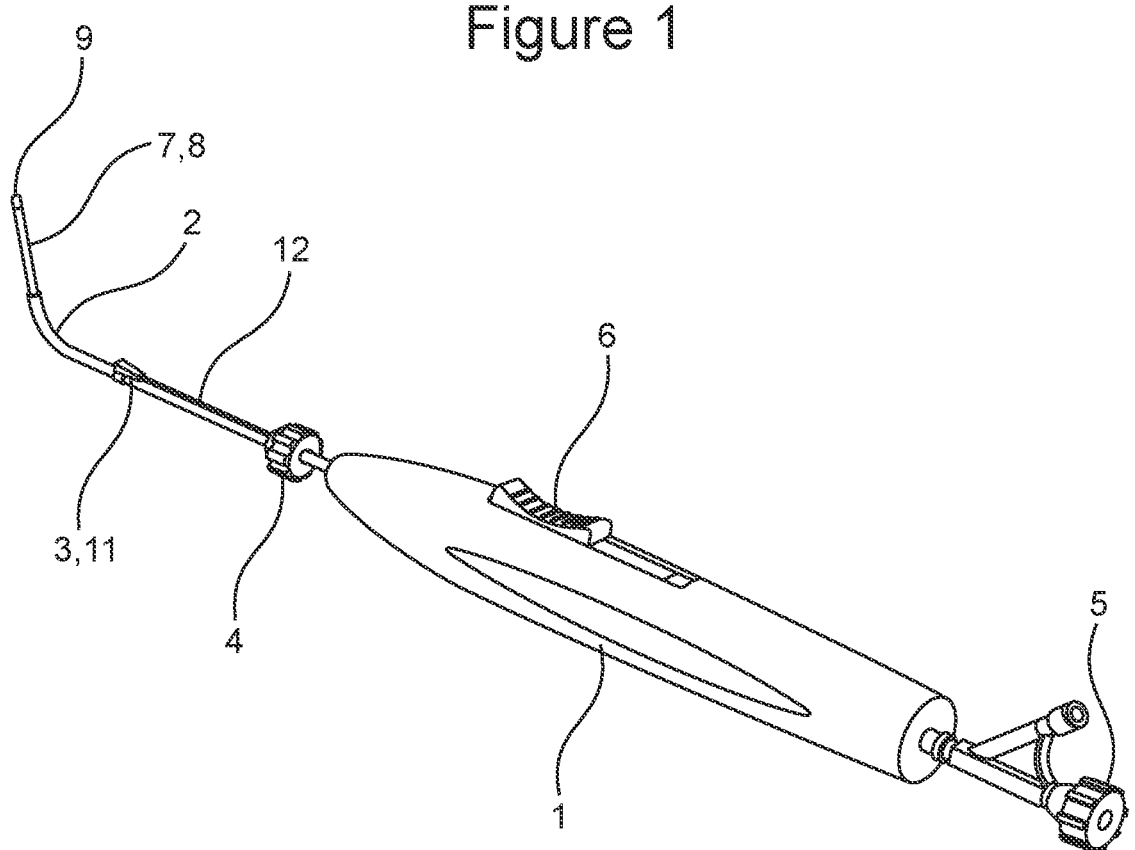
FIG. 2A is an illustration of the device of the present invention with the protective sleeve and dilating element extended.
Figure 2B:
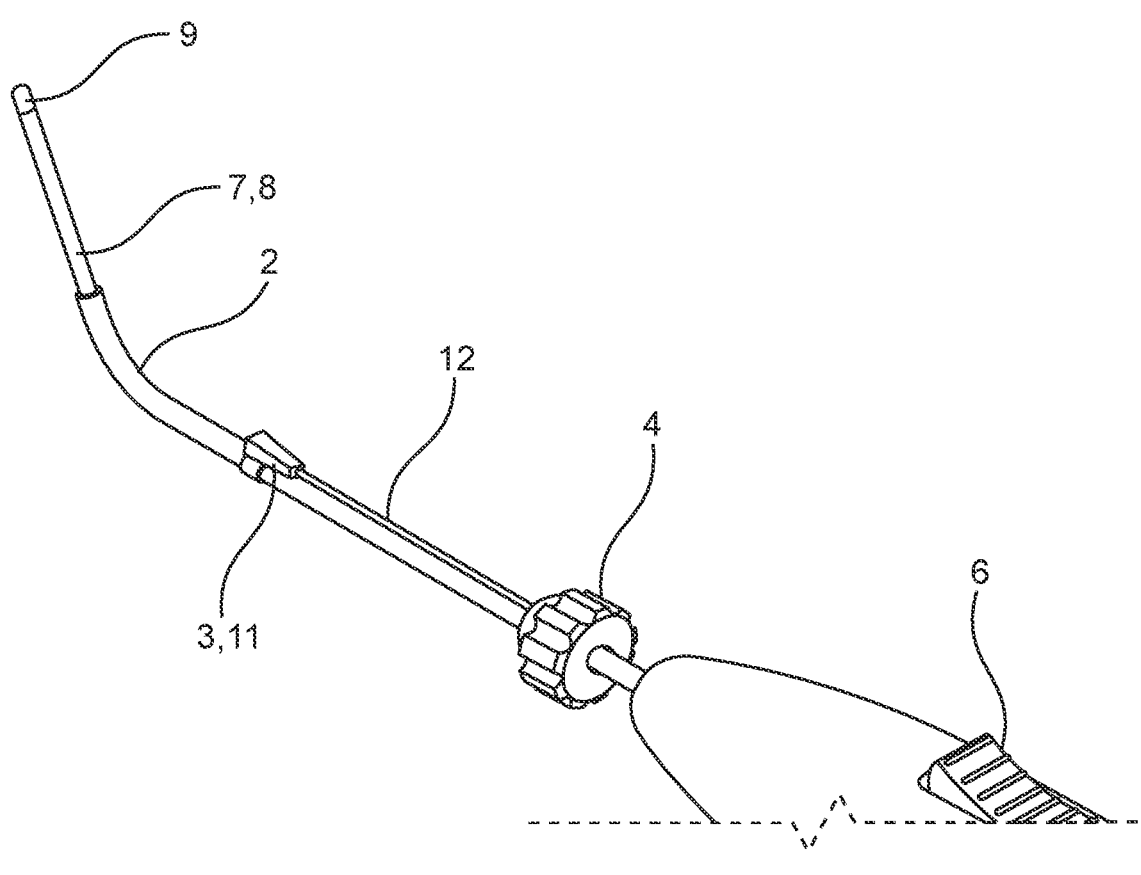
FIG. 2B is an enlarged view of the distal end of the device in FIG. 2A.

As seen in FIG. 2A, the protective sleeve 7 with compressed or collapsed dilator 8 inside is extended from the insertion tube 2 at the opening 36 at the tube distal end 38. Also indicated in FIG. 2A is an atraumatic tip 9, which is the distal tip of the dilating element 8. The atraumatic tip 9 assures easy and safe insertion of the dilator and the protective sleeve into the eustachian tube of the patient by preventing possible perforation of the eustachian tube wall. An enlarged view of this is provided by FIG. 2B, indicating the protective sleeve 7 with dilator 8 extending from and beyond the distal end 38 of bent section of the insertion tube 2. The atraumatic tip 9 is also seen attached to the dilator 8.

In FIG. 2A, it is also seen that the dilator control slider 6 slides from the first position that was shown in FIG. 1 to a second position which is forward in the slot 40 on the cylindrical body of the main handle. This repositioning and movement of the slider 6 moves the protective sleeve 7 and expandable dilator 8 from inside the insertion tube 2 to an external position outside the insertion tube 2 by moving the sleeve 7 and dilator 8 out of opening 36 on the insertion tube 2. In the external position, as described herein, the collapsible dilator 8 will have the ability to expand upon the removal of the protective sleeve, and thereby push open and hold open surrounding tissue in a treatment area of a patient, such as a eustachian tube.

Figure 3A:
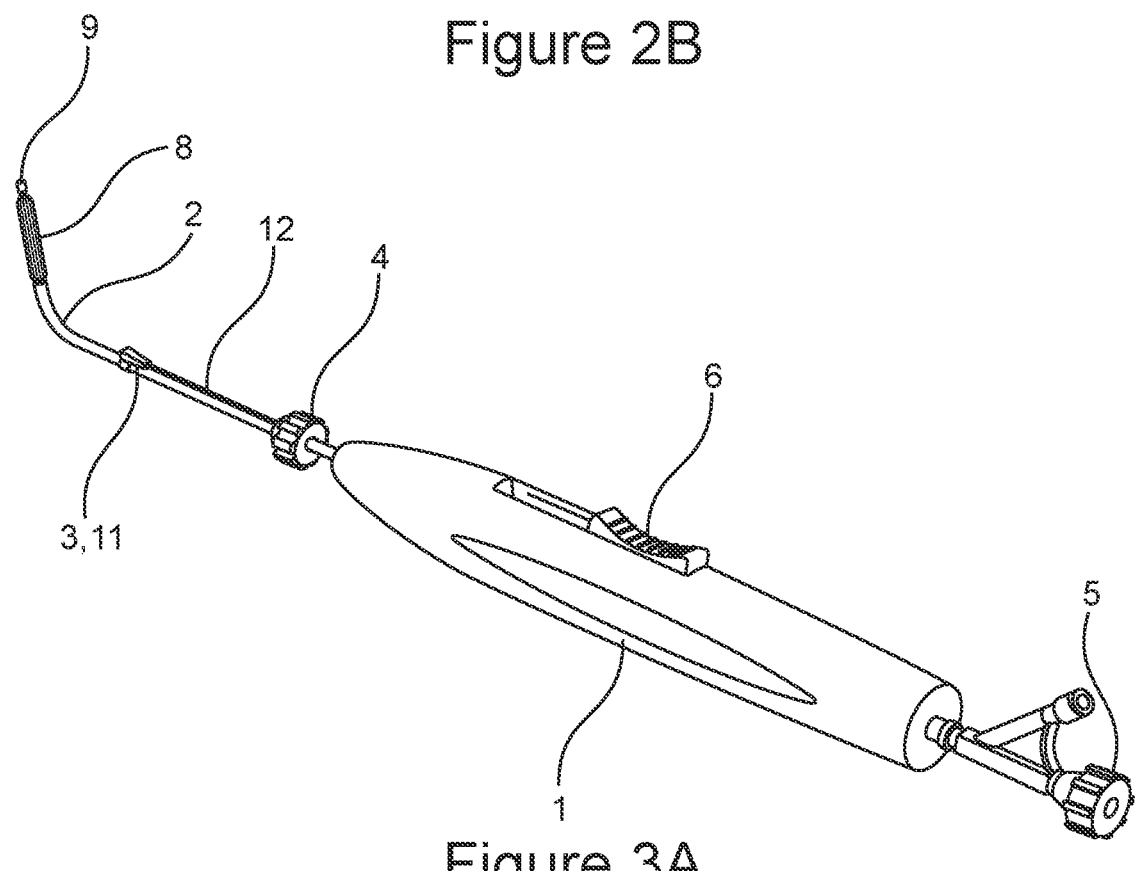
FIG. 3A is an illustration of the device of the present invention with the dilating element opened.
Figure 3B:
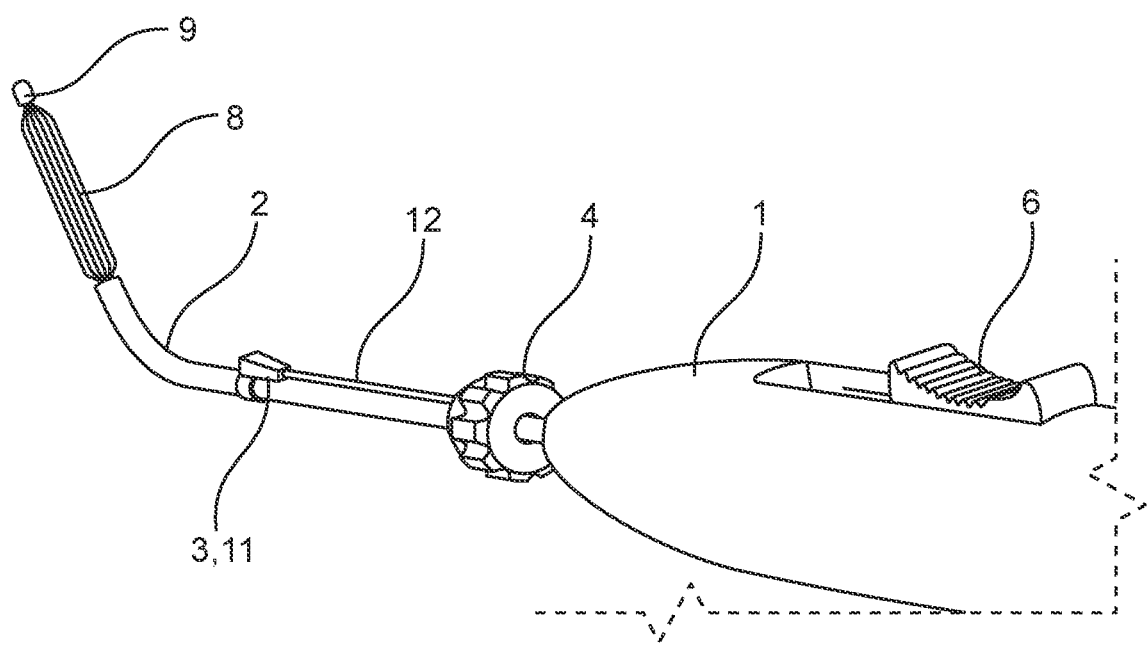
FIG. 3B is an enlarged view of the distal end of FIG. 3A.
Figure 3C:
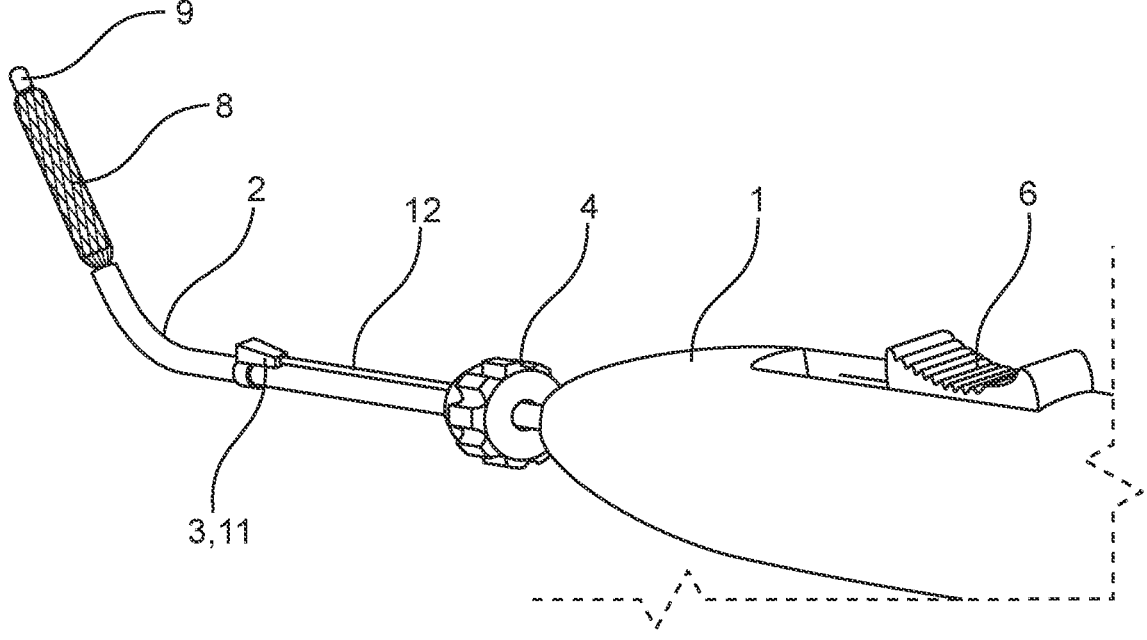
FIG. 3C is an enlarged view of the distal end of FIG. 3A with a different type of dilating element.

In FIG. 3A and FIG. 3B, there is shown the device 100 of the present invention with the dilator control slider 6 moved back to a first position. By moving the position of the slider 6 back, the protective sleeve 7 is pulled back and retracted back inside the insertion tube 2, leaving the dilator 8 exposed and expanded. The dilator 8 can expand to a diameter beyond the diameter of the insertion tube 2 and the protective sleeve 7 in order to prop open the surrounding tissue area which then allows for treatment, examination, or other medical procedures. It should also be noted that alternatively, a middle position can be set for the dilator control slide 6 to pull back and remove the protective sleeve 7 from the dilator 8 to expose and expand the dilator 8. The dilator 8 in FIG. 3B is shown as a plurality of straight wire-type components fastened at and running from the inside of the insertion tube 2 to the inside or underside of the atraumatic tip 9 in a manner parallel to the axis of the insertion tube 2. The wires used for the dilator may be Nitinol or other metal or polymer type wires. When the dilator 8 is expanded, it creates an open slotted basket which maintains the tissue open for medical procedure, such as treatment of the eustachian tube. In the FIGS. 3A and 3B, this is shown as the multiple straight parallel wires forming the expanded open basket dilator 8. In FIG. 3C, there is shown a different embodiment of the dilator 8 where the expanded basket is a cross hatched mesh design of wires or other suitable structure or material, which again creates an open basket type structure for providing an outward force away from the dilator to support and expose the surrounding tissue.

In an embodiment, the dilator 8 is a stent like scaffold component which has a memory shape which expands and dilates when the protective sleeve 7 slides off the dilator 8 and is pulled back into the insertion tube 2. Additionally, in an embodiment, the dilator 8 has one of the ends of the dilator 8, (either proximal or distal) which is pushed, pulled or rotated in order to expand the dilator 8 in an Oriental lantern type pattern or shape, and can include protruding edges or tabs on the wires for further support on the tissue. The above examples are not limiting, as other shapes for the dilator 8 are within the scope of the present invention.

Figure 4A:
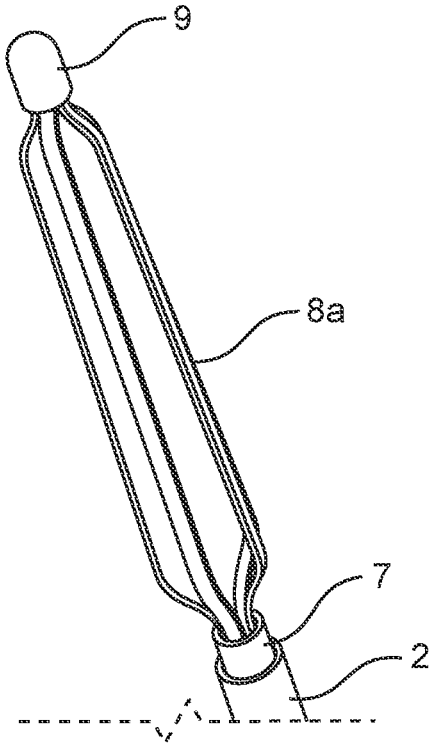
FIG. 4A is an enlarged view of the dilating element of FIGS. 3A and 3B.
Figure 4B:
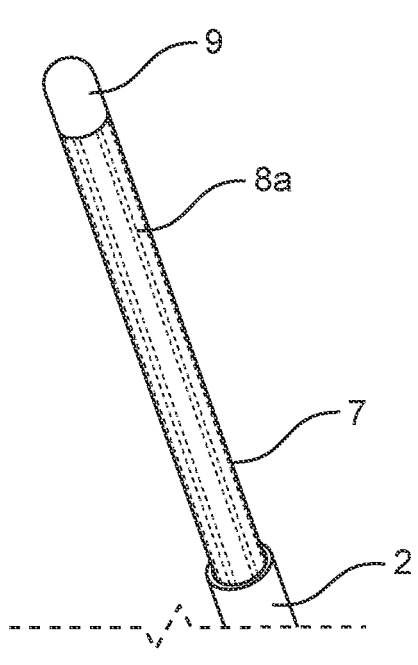
FIG. 4B is an illustration of the dilating element of FIG. 4A covered by the protective sleeve.

In FIGS. 4A and 4B, there are enlarged views of the distal end of the insertion tube 2 with the dilator 8. In FIG. 4A, there is seen an expanded dilator 8, with individual expanded and separated bladed or wires 8a with open space in between each of the blades or wires 8a. As shown, the blades 8a are flat on an outer surface, but other shapes are within the scope of the invention. The protective sleeve 7 is also shown protruding from the opening 36 at the end of insertion tube 2. The blades 8*a* of the dilator 8 extend from inside the sleeve 7 up to the inside of the atraumatic tip 9. In FIG. 4B, the protective sleeve 7 has moved forward again to cover the dilator 8 and collapse the dilator 8 inside the sleeve 7 to protect the tissue. The collapsed dilator arms or blades 8*a* are seen within the sleeve 7 as dotted lines in FIG. 4B. The protective sleeve 7 extends fully over the dilator 8 and contacts the base of the atraumatic tip 9 of the dilator 8 to form a single outer surface. In this manner, the sleeve 7 protects the tissue, such as eustachian tube mucosa, by preventing direct contact between the dilator structure and the sounding tissue during the pull back of the dilator 8 into the insertion tube 2. Upon completing the pull back of the protective sleeve 7 with the dilator 8 in it into the insertion tube 2, the device can be safely withdrawn and removed from (and inserted to) the patient's nose.

Figure 5A:
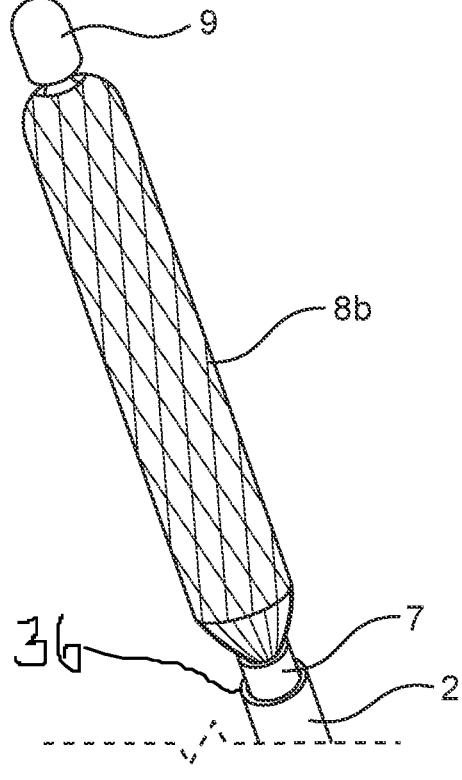
FIG. 5A is an enlarged view of the dilating element of FIG. 3C.
Figure 5B:
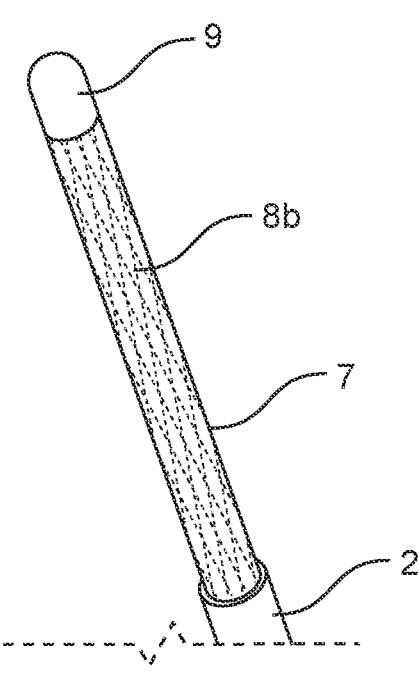
FIG. 5B is an illustration of the dilating element of FIG. 5A covered by the protective sleeve.

FIGS. 5A and 5B are similar to FIGS. 4A and 4B described above, but with the dilator 8 having the cross-hatching mesh structure wire design Sb as previously indicated in FIG. 3C. In FIG. 5A, there is again seen an expanded dilator 8, with an expanded and separated mesh design 8*b* with open space in between each of the individual mesh wires. The protective sleeve 7 is also shown protruding from the opening 36 at the end of insertion tube 2, The mesh frame 8*b* of the dilator 8 extends again from inside the sleeve 7 up to the atraumatic tip 9, forming an basket shape with openings between the cross hatched mesh. In FIG. 5B, the protective sleeve 7 has moved forward again to cover the dilator 8 and collapse the dilator 8 inside the sleeve 7 to protect the tissue. The collapsed dilator mesh structure 8*b* is seen within the sleeve 7 as dotted lines in FIG. 5B. The protective sleeve 7 extends fully over the dilator 8 and contacts the base of the atraumatic tip 9 to form a single outer surface. Once again, the sleeve 7 protects the tissue, such as eustachian tube mucosa, from potential harm by the dilator 8 when the dilator is being withdrawn from the eustachian tube into the insertion tube 2. Upon withdrawing the protective sleeve with the dilator in it all the way into the insertion tube 2, the device is being withdrawn from (and inserted to) the patient's nose.

Figures 6A, 6B:
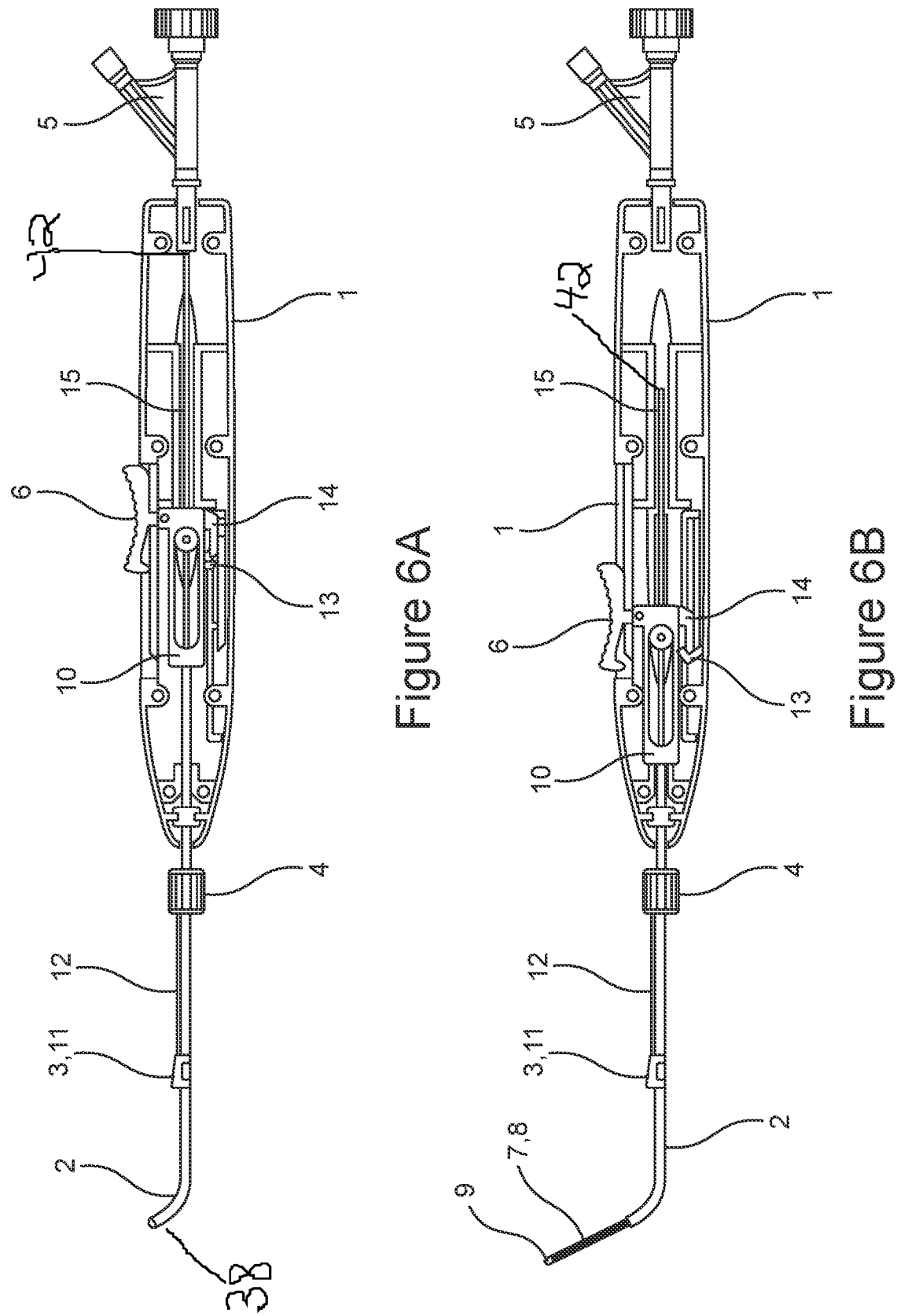
FIG. 6A is a cross section view of the device of the present invention in a first position with the dilating element and the protective sleeve retracted.
FIG. 6B is a cross section view of the device of the present invention in a second position with the dilator extended and covered by the protective sleeve.

In FIGS. 6A through 6E, there are shown cross sections of the present invention at each stage of the use and operation of the invention. In FIG. 6A, there is shown the initial position of the dilator control slider 6. In the cross-sectional view, it can be seen that the dilator control slider 6 is connected to an internal plate 10 which slides along an internal shaft 15. The internal plate 10 is connected to the protective sleeve 7, which covers the dilator 8. A latch 13 is also connected to the internal shaft 15, which is connected to the dilator 8 at the distal end of shaft 15. The dilator control slider 6 is also connected with pin 14 which activates latch 13. In the configuration shown in FIG. 6A where the protective sleeve 7 and the dilator 8 are inside the insertion tube 2 the device is inserted into the patient's nose.

In FIG. 6B, the dilator control slider 6 has been moved forward to a second position. The slider 6 is connected mechanically to the internal plate 10, which as stated above, is connected to the protective sleeve 7. In this manner, the slider 6 moves the internal plate 10 forward as well as latch 13 and pin 14. The assembly of the plate 10, latch 13 and pin 14 are aligned on internal shaft 15 which moves forward when slider 6 is moved from the initial position shown in FIG. 6A to the second position shown in FIG. 6B. The internal shaft 15 is moved forward from its initial position (where the proximal end 42 of the internal shaft 15 is in contact with the port 5 end that is internal to the device 100) to a second position. As the shaft 15 and plate 10 move forward, the protective sleeve 7 with dilator 8 inside and its atraumatic tip 9 moves forward and extends from the end of the insertion tube 2 to a position external to the insertion tube 2. This allows the medical professional to insert and position the dilator 8 safely inside the eustachian tube for treatment or examination without irritating or injuring the eustachian tube wall.

Figures 6C, 6D:
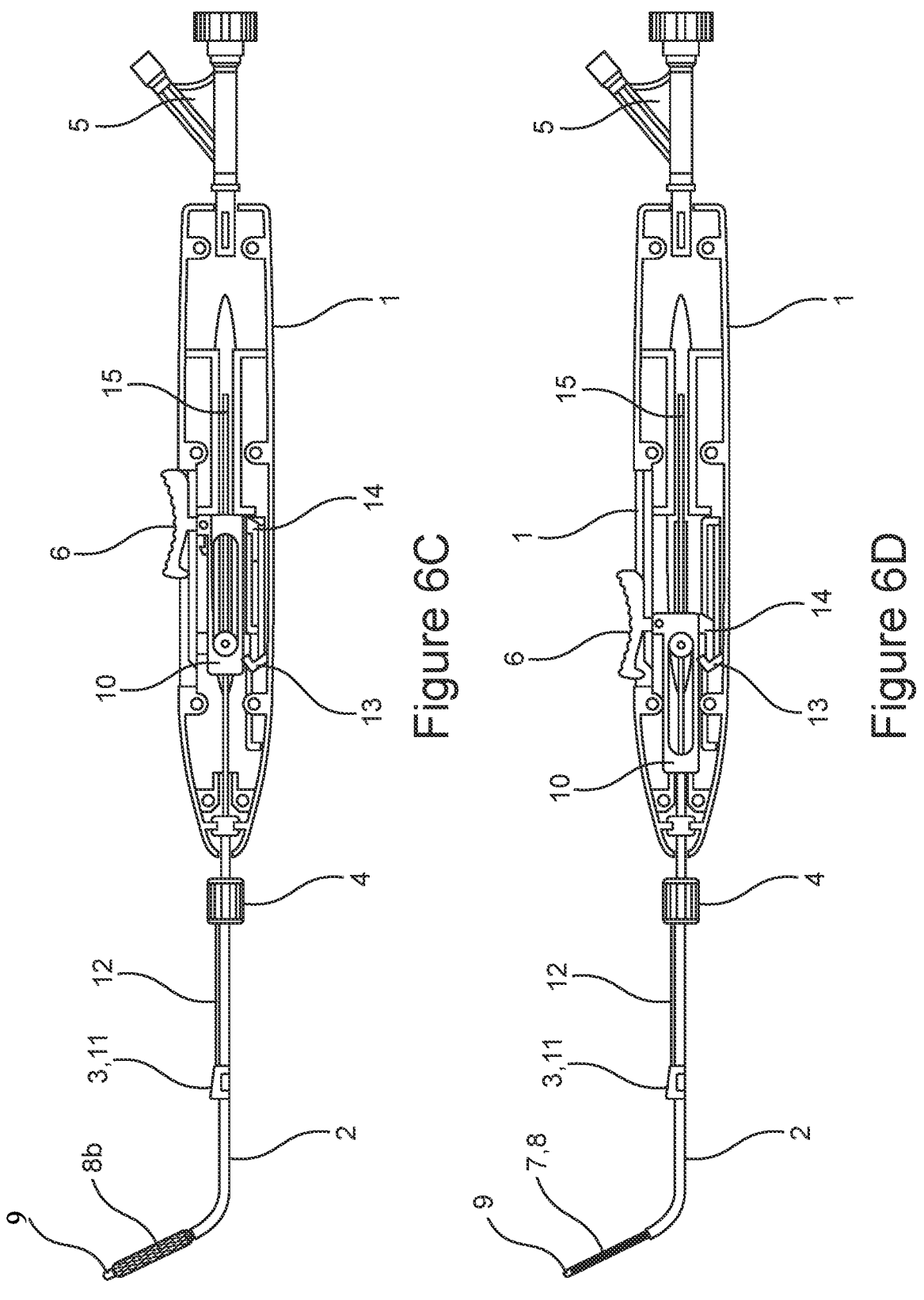
FIG. 6C is a cross section view of the device of the present invention with the dilating element extended and opened.
FIG. 6D is a cross section view of the device of the present invention with the dilating element extended and covered by the sleeve.

In FIG. 6C, the dilator control slide 6 is brought back to its initial position again and the internal plate 10 moves back as well. This time, as the slide 6 is moved back, the latch 13 remains at the advanced forward position and only the pin 14 returns to the back (proximal) position. This action pulls the protective sleeve 7 off the dilator 8 and back into the insertion tube 2. The dilator 8*b* is allowed to expand outward and keeps the eustachian tube walls open during a procedure or examination.

In FIG. 6D, the dilator control slide 6 is moved forward again, which moves the internal plate 10 forward as well. The pin 14, connected to the plate 10, moves forward to contact latch 13 again. As the pin 14 and plate 10 move forward, this moves the protective sleeve 7 over the opened and extended dilator 8 and collapses the dilator 8 within the protective sleeve 7. The sleeve 7 and dilator 8 inside it may now be safely removed from the eustachian tube without injuring the sounding tissue area as the medical professional withdraw them back inside the insertion tube 2.

Figure 6E:
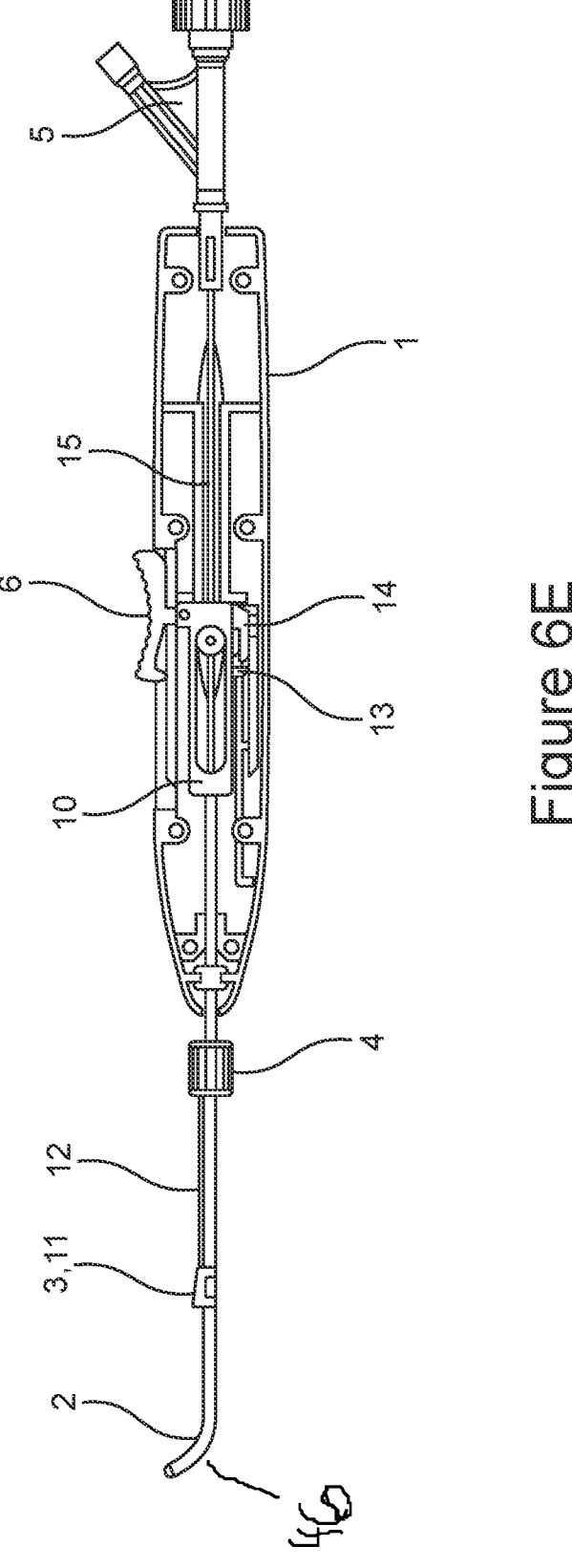
FIG. 6E is a cross section view of the device of the present invention with the dilating element and the protective sleeve retracted.

In FIG. 6E, the dilator control slide 6 is moved back to the initial position. This returns the internal plate 10 back to its initial position and the internal shaft 15 is also brought back to the position of contact and connection with port 5. The dilator 8 and the protective sleeve 7 around it are drawn back inside of the insertion tube 2. The insertion tube 2 and device may be safely removed from the patient.

Figure 7:
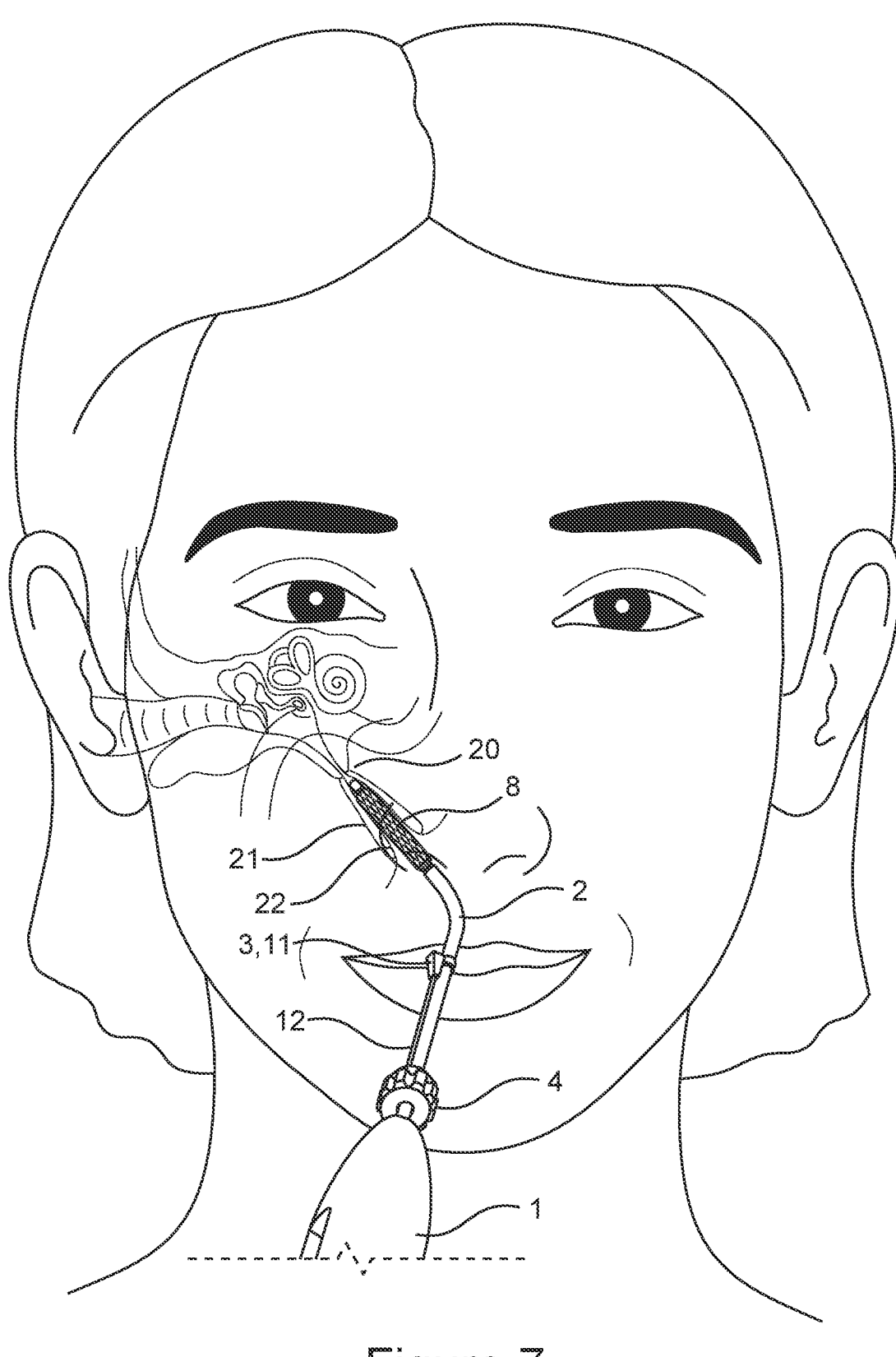
FIG. 7 is an illustration of the present invention in use on a patient.

Referring to FIG. 7, there is shown the present invention in use on a patient. The device 100 is inserted into a patient's nostril 22 with the insertion tube 2 indicated with curved section 46 bending in toward the patient's nose and the expanded dilator 8 (the cross hatched mesh design shown, but other designs are applicable). The distal tip of dilator 8 is inserted up to the isthmus 20. The expanded dilator 8 is pushing open the eustachian tube walls 21 cartilage and 22 mucosa. With the eustachian tube walls 21, 22 held open by the dilator 8, the medical professional is able to perform treatments, procedures and examinations on the desired area.

In use, the first step is inserting the eustachian tube therapeutic device 100 into the patient's nose. The insertion tube 2 of the eustachian tube therapeutic device 100 is inserted trans-nasally until the distal tip 38 reaches the opening of the eustachian tube. An optional imaging module comprises an imaging sensor (around 1 mm×1 mm, typically CMOS) and illumination means (a light guiding or emitting means such as fiber optic or at least one LED) that are mounted in the camera housing 3.

The imaging module with camera housing 3 is attached (mounted/latched) onto the insertion tube 2 in at least one point. The imaging module can be slide back and forth along the insertion tube 2 by the camera controlling knob 4 to get it closer to the treated site for a closer view, or further back to get a wider field of view. Optionally, the imaging module can also be rotated around the insertion tube 2 by the camera controlling knob 4 to adjust the image orientation. Upon the distal tip of the insertion tube 2 reaching the opening of the eustachian tube, the dilator control slider 6 is pushed forward.

The next step of the process is intubating the eustachian tube. Pushing the slider 6 forward extends outward and inserts the folded closed/collapsed dilator 8, which is located inside its protective tube/sleeve 7, into the eustachian tube. The slider is pushed all the way forward until the atraumatic distal tip of the dilator 9 reaches the isthmus.

Next, in the process, the present invention is used for dilating and delivering therapeutic means. As soon as the distal atraumatic tip 9 reaches the tympanic isthmus, the slider 6 is pulled backward. This pulls backwards the dilator protective tube/sleeve 7 into the insertion tube 2. The main purpose of the dilator protective tube/sleeve 7 is to buffer between the structural ribs of the dilator 8 and the mucosa folds to prevent possible mucosa injury during the dilator 8 sliding forward and backward against the mucosa. The dilator 8 with its open structure allows for direct access of injected drug to the mucosa. The dilator 8 with its open structure allows for suction and removal of secretion from the eustachian tube. The dilator 8 design can be shaped as a basket or a whisk (shown and described in FIG. 4A above), or a stent-like (shown and described in FIG. 4B above). The dilator 8 can optionally be left in the eustachian tube for a certain period, including several hours or even days. The dilator may optionally be drug-eluting consisting of a metallic scaffold, a polymer coating (which may be durable or bioresorbable), drug that is mixed within the polymer and released over a period of time. The dilator 8 can optionally contain certain sensors including a camera or biosensors.

By pulling back the dilator protecting tube/sleeve 7, the medical professional exposes the dilator 8 and allows the dilator 8 to expend outward and dilate the mucosa folds of the eustachian tube. As soon as the dilator protective tube/sleeve 7 is retreated completely into the insertion tube 2, and the dilator 8 is extended, dilating the mucosa, the physician can start the therapeutic phase by connecting any delivery means (i.e. syringe, canister, etc.) to the delivery port 5. The physician may deliver through the delivery port 5 any therapeutic means, for example antibiotics, steroids, surfactant, saline, or alternatively a drug eluting wick can be inserted inside the dilator 8. In another option, the physician can insert into the delivery port 5 a fiber laser diffuser through the entire eustachian tube therapeutic device 100, through the open dilator 8 and all the way up to the atraumatic distal tip 9 of the dilator 8. Then the physician may activate the laser with a certain wavelength such as 940 nm for a period of time for anti-inflammatory treatment and then turn the laser off. The physician can also use suction through port 5 to remove secretion from the eustachian tube.

After treatment, the physician removes the eustachian tube therapeutic device 100. When the physician is ready to remove the eustachian tube therapeutic device out from the patient's nose, the slider 6 is pushed all the way forward. By sliding the slider 6 forward, this extends the dilator protective tube/sleeve 7 out from the insertion tube 2. The dilator protective tube/sleeve 7 slides over the dilator 8 and folds (collapses) it into the dilator protective tube/sleeve 7. When the dilator protective tube/sleeve 7 is all the way out, covering entirely the folded dilator 8, the sleeve 7 buffers between the dilator 8 and the mucosa to prevent injury.

The slider 6 is then pulled back all the way to pull the dilator 8 and its dilator protective tube/sleeve 7 out from the eustachian tube and into the insertion tube 2. When the dilator 8 and the dilator protective tube 7 are out from the eustachian tube and inside the insertion tube 2, the insertion tube 2 is safely pulled outward from the patient's nose.

The present invention is designed to expose many structures in the back of the nose. Other target organs and structures which may be accessed in the back of the nose with the present invention include, but are not limited to: posterior turbinates, posterior nasal septum, nasopharynx, choana, palate and palate muscles, eustachian tube, sphenoid sinus, posterior ethmoid sinus, cavernous sinus, the skull base, clivus, upper cervical spine.

The present invention can deliver therapeutic medication and/or laser energy delivery to the desired area, and also allow for injecting medication directly to, or removing secretion from, the desired areas of treatment by opening up the eustachian tube.

As shown in FIGS. 8 through 13, there is shown another embodiment of the device of the present invention for treatment of eustachian tube dysfunction. In FIGS. 8A and 8B, there is again shown a handle section 115 with an insertion tube 112 extending from the handle section 115. The insertion tube 112 is thinner than the handle section 115, and is rigid. As shown in FIG. 8A, a curve toward the distal end, which may be adjusted by the medical professional, assists in positioning the insertion tube 112 inside a patient's nostril during a procedure. The dilator distal atraumatic tip 110 is shown protruding from the insertion tube 112 distal end. Along the surface of the insertion tube 112 is the optional camera 113, the camera control knob 114 and a mechanical link/connection 116 between the camera 113 and the camera control and manipulation knob 114. A camera cable may run inside the mechanical link 116. The dilator 111 and its protective sleeve 124 are contained inside of the insertion tube 112 and will extend outward from the insertion tube 112 during use of the device. (See, FIGS. 9-10).

Figures 8A, 8B:
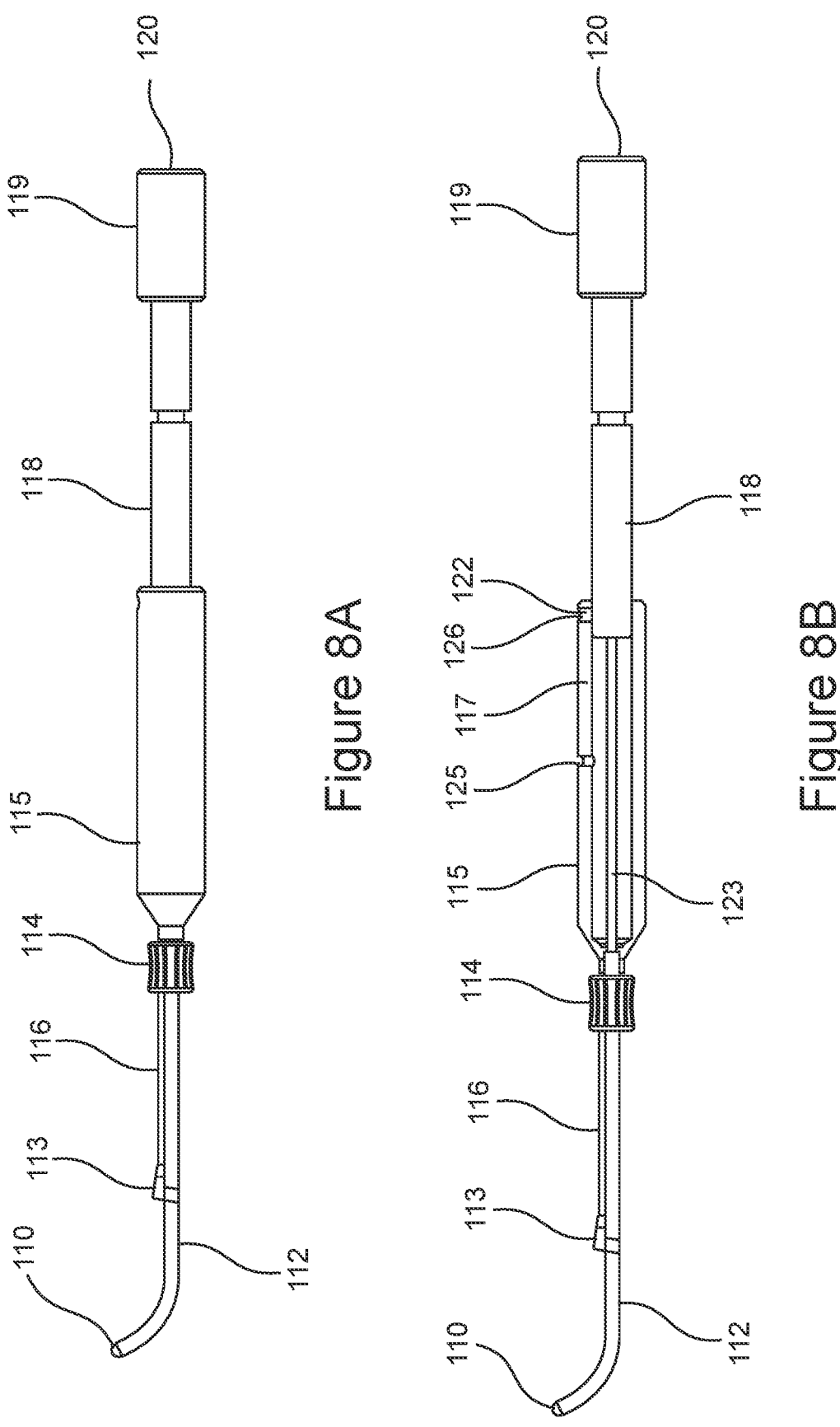
FIG. 8A is an illustration of an embodiment of the present invention.
FIG. 8B is an illustration of an embodiment of the present invention.

At the proximal end of handle section 115 is the inner slider piece 118, which is positioned inside of handle 115 and extends out from the proximal end of handle 115. In FIGS. 8A and 8B, the inner slider 118 is pulled out from the handle section 115 to its fully extended initial position. The inner slider 118 is connected to the dilator 111 inside of the handle section 115 by shaft 123. (FIG. 8B). The inner slider piece is a cylindrical shaped piece, but other shapes are within the scope of the invention. At the other end of the slider piece 118 is the outer slider piece 119. Attached to the proximal end of the outer slider piece 119 is a working channel port 120 to deliver therapeutic means (surfactant, drugs, laser fiber, etc.) to the dilator 8. Optionally, the working channel port 120 is a Luer Lock connector. The entire device and each of the pieces (handle section, inner slider piece, outer slider piece, tube) described herein are removable and disposable.

In FIG. 8B, the internal connections of the device are shown. The inner slider 118 is shown positioned inside the hollow, cylindrical handle section 115 connecting with shaft 123 which is extends for the internal length of the handle section 115. The shaft 123 connects with dilator 111 which is inside of insertion tube 112. Also shown in FIG. 8B is the latching pin 122, the forward stopper 125 of the handle sliding groove 117, and the rear stopper 126 of the handle sliding groove. The handle sliding groove 117 allows the latching pin 122 to slide forward up to the forward stopper 125 and to slide backward to the rear stopper 126. The latching pin 122 is rotated, (clockwise is shown), into the forward stopper 125 to latch the inner slider 118 which is connected to the dilator 111 via shaft 123. This allows the user to pull back the outer slider piece 119 in order to retreat and withdraw the protective sleeve 124 into the insertion tube 112. The withdrawal of the protective sleeve 124 exposes and allows the dilator 111 to open and expand outward.

Figures 8C, 8D:
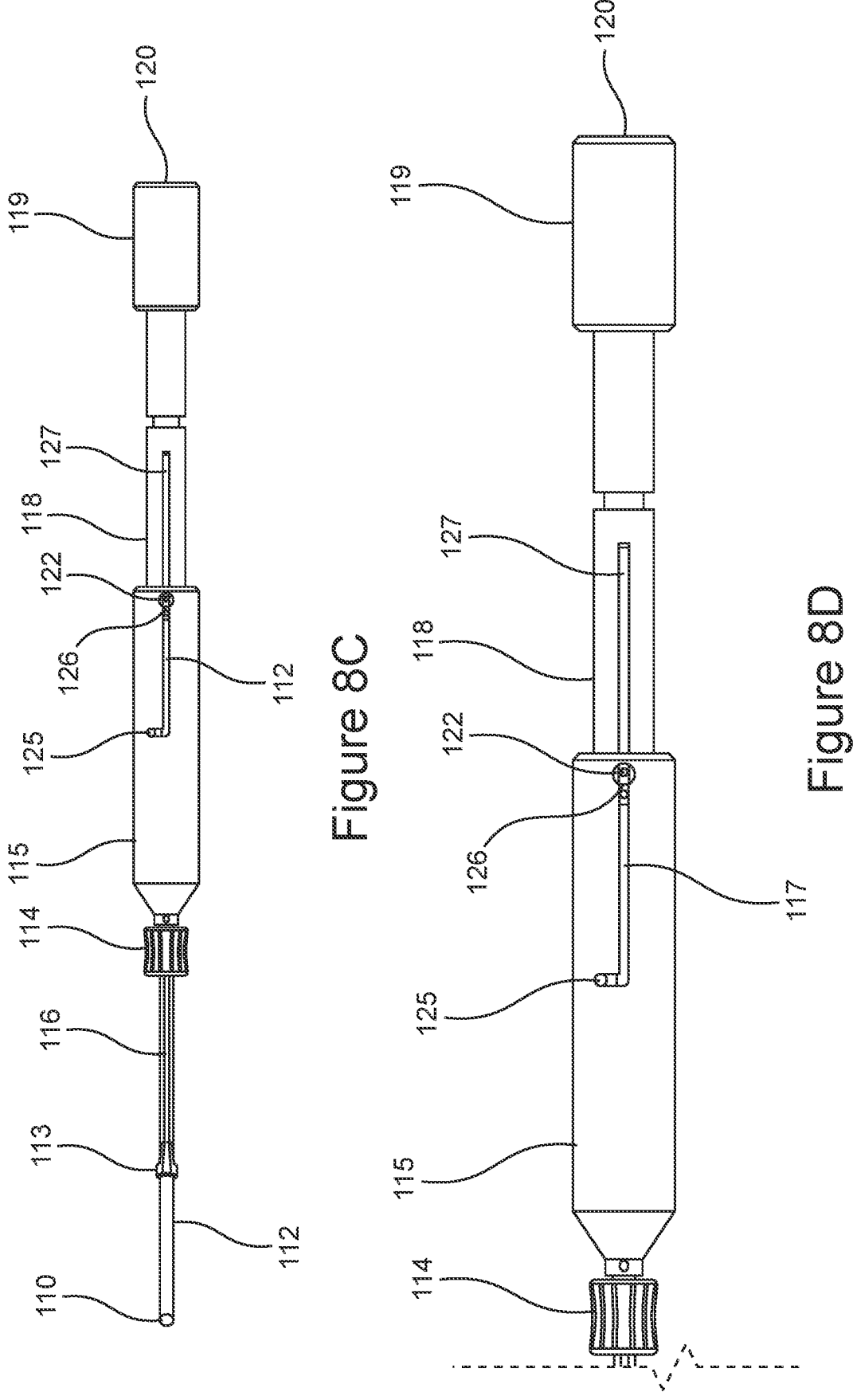
FIG. 8C is an illustration of an embodiment of the present invention.
FIG. 8D is an illustration of an embodiment of the present invention

This can be seen further in FIGS. 8C, and the enlarged version in 8D, which show a top view of the latching pin 122, forward stopper 125, the rear stopper 126, the handle sliding groove 117 and the slot 127 on the inner slider 118. The latching pin 122 is shown in position against the rear stopper 126 within the handle sliding groove 117. The forward stopper 125 is shown at the other end of the handle sliding grove 117, with a slight offset from the edge of the groove 117 to move the forward stopper 125 off the handle groove 117. With the inner slider 118 retracted back and partially extending from the rear of the handle section 115, the latching pin 122 is moved against the rear stopper 126. The slot 127 on the inner slider 118 is also seen in FIGS. 8C and 8D, which allows the inner slider 118 to move across the latching pin 122 when the inner slider 118 is moved between positions, sliding in and out of the handle section 115.

Figures 9A, 9B:
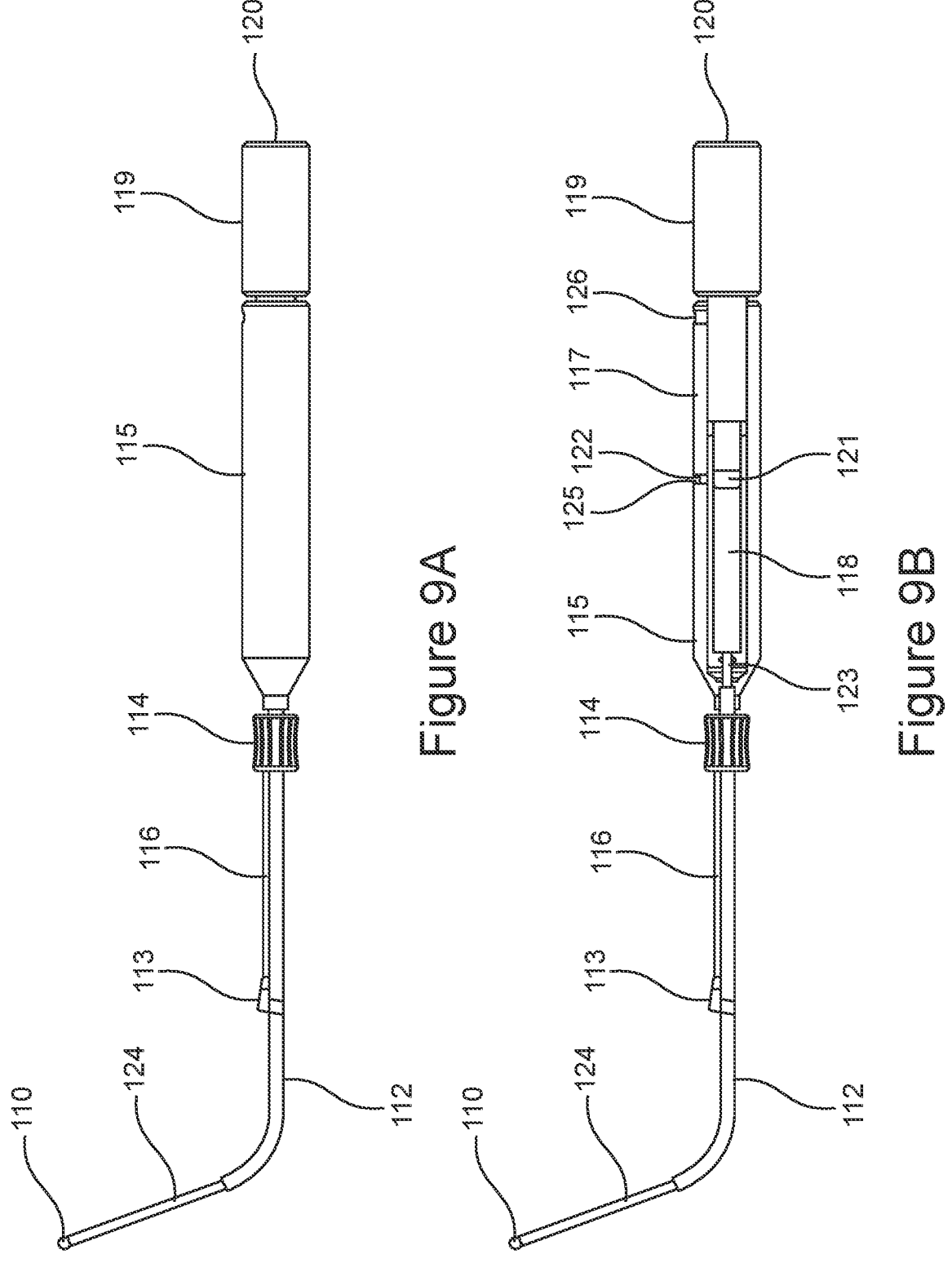
FIG. 9A is an illustration of an embodiment of the present invention.
FIG. 9B is an illustration of an embodiment of the present invention.

Referring to FIGS. 9A through 9D, there is shown the device of the invention with the inner slider 118 moved to its internal position inside the handle section 115. The device with the collapsed inner slider is shown in FIG. 9A, where only the outer slider 119 is visible. By moving the inner slider 118, the internal shaft 123 is pushed forward as shown to the distal end of the handle section 115. The protective sleeve 124 with the collapsed dilator 111 in it are also pushed forward and extend beyond the insertion tube 112 for the desired distance to reach the treatment area without injury to surrounding tissue of the patient. The atraumatic tip 110 at the distal end of the dilator 111 also protects against tissue injury and possible perforation of the surrounding wall of the tube in this process. Once the dilator 111 and the protective sleeve 124 are in appropriate position, the protective sleeve 124 is withdrawn and allows for the dilator 111 to open inside of the eustachian tube and expand its mucosa folds.

Figures 9C, 9D:
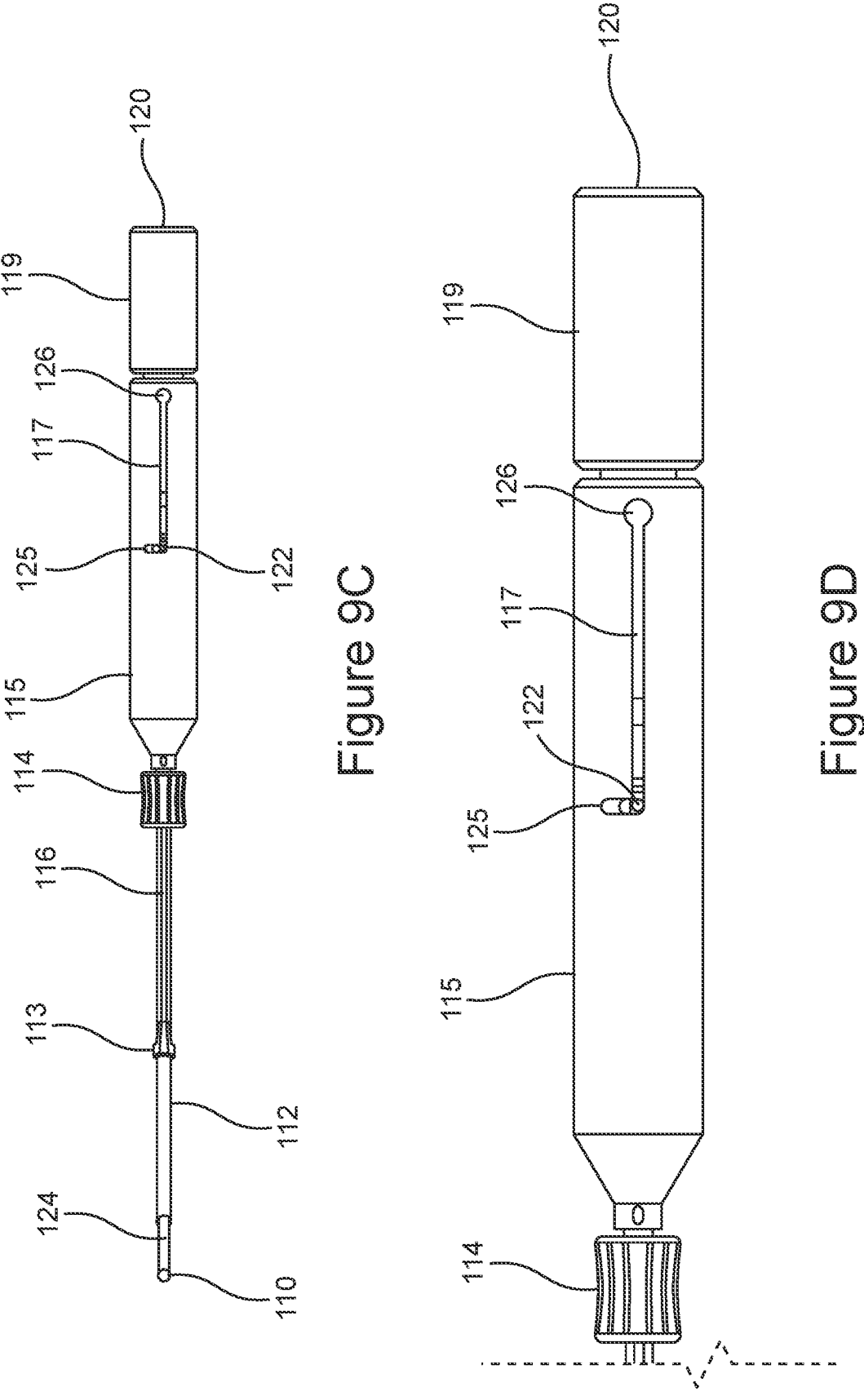
FIG. 9C is an illustration of an embodiment of the present invention.
FIG. 9D is an illustration of an embodiment of the present invention.

As seen in FIG. 9B, there is the latching pin 122 in position against the forward stopper 125, with the rear stopper 126 at the proximal end of handle section 115. Beneath the latching pin 122 and forward stopper 125 is shown a ring 121. The ring 121 is the connection which links between the inner slider piece 118 and the shaft 123. FIGS. 9C and 9D (enlarged view of FIG. 9C) are top views of the present invention with the outer slider 119 fully compressed against the handle section 115 and the inner slider 118 fully pushed internal to the handle section 115. The latching pin 122 and forward stopper 125 are shown next to each other in the handle sliding groove 117.

Figures 10A, 10B:
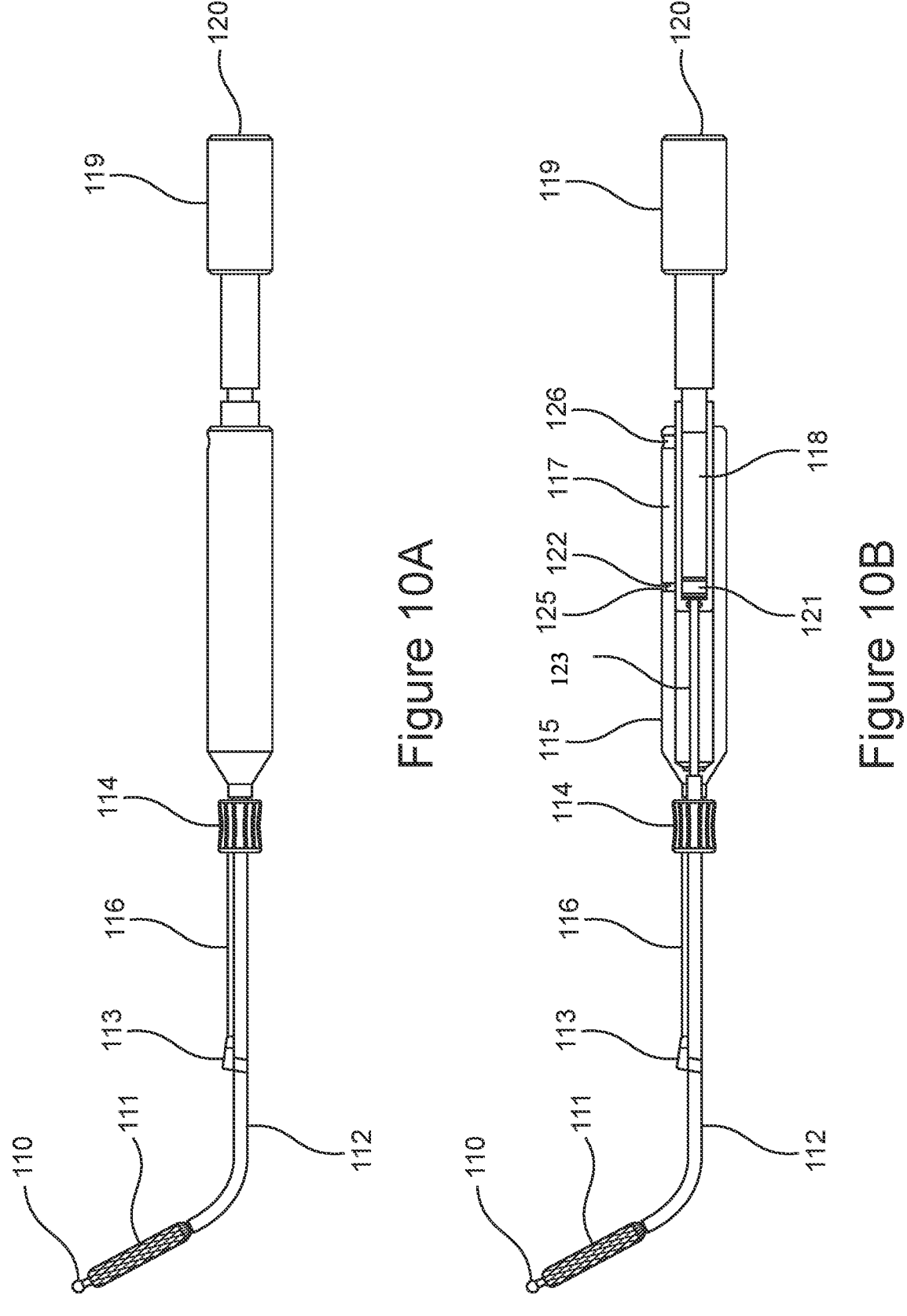
FIG. 10A is an illustration of an embodiment of the present invention.
FIG. 10B is an illustration of an embodiment of the present invention.
Figure 10C:
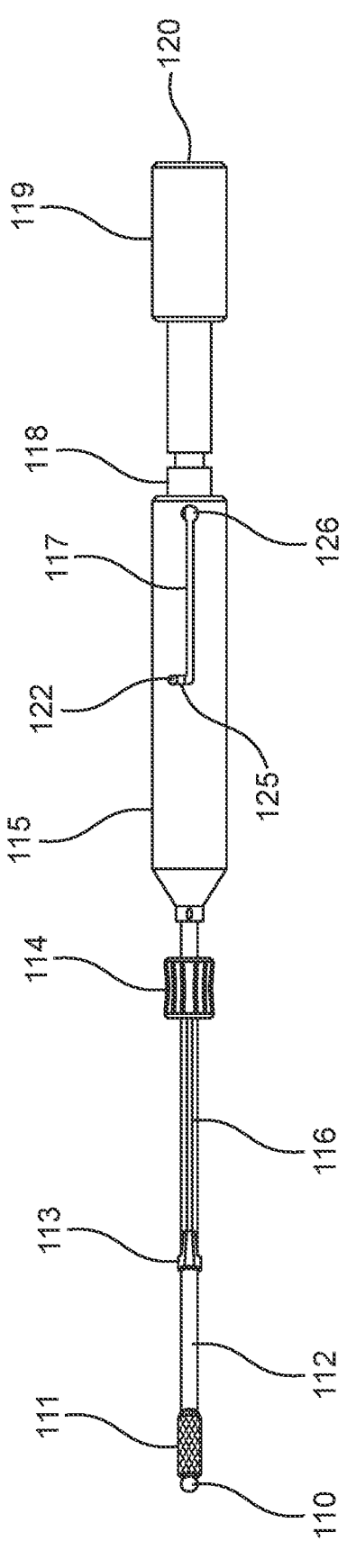
FIG. 10C is an illustration of an embodiment of the present invention.
Figure 10D:
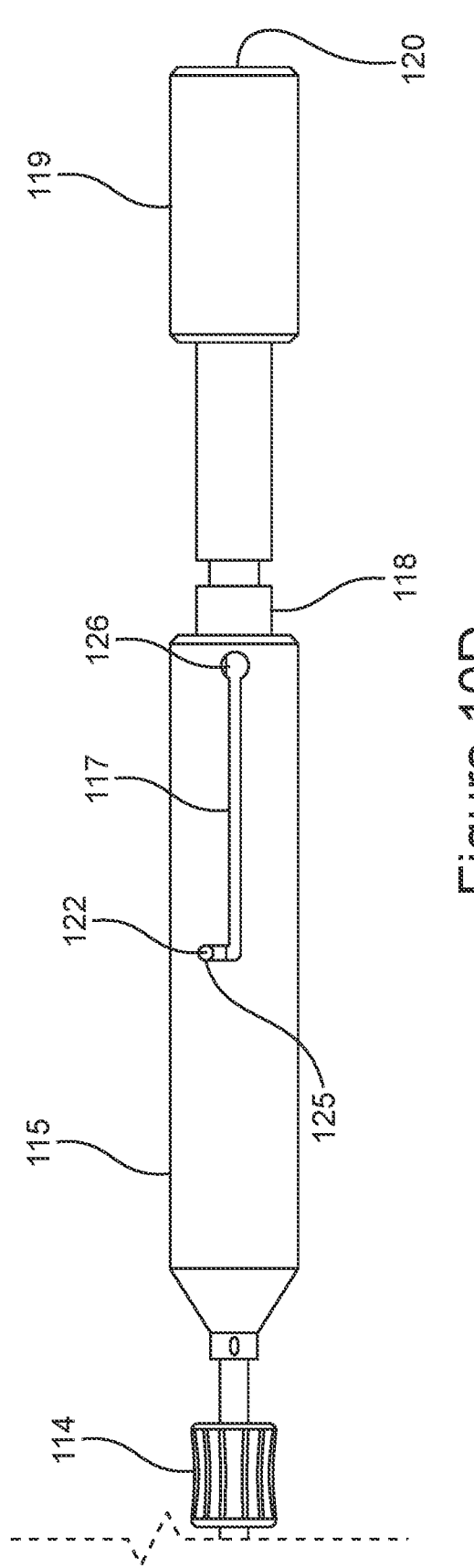
FIG. 10D is an illustration of an embodiment of the present invention.

Referring to FIGS. 10A through 10D, there is shown the outer slider piece 119 pulled back so that the protective sleeve 124 slides off the dilator 111 and is retracted in the insertion tube 112. In this manner, the collapsed dilator 111 becomes exposed and expands external to the insertion tube 112. The shaft 123 is pulled back as shown in FIG. 10B. The latching pin 122 remains at the forward stopper 125 position with ring 121. With the protective sleeve 124 retracted, the basket style or stent-like dilator 111 expands to open the tissue of the eustachian tube and maintains the tissue open during procedures. FIGS. 10C and 10D are top views of the device of the present invention in this position with the dilator 111 extended and expanded. The latching pin 122 and forward stopper 125 are shown in position. The camera control knob 114 and camera 113 can be used to assist the medical professional in the procedure.

Overall, the dilator 111 with its protective sleeve 124 are in the insertion tube 112 to start. Then, the outer slider 119 pushes outward the dilator 111 and its protective sleeve 124. In the next position, the dilator 111 is exposed after the outer slider 119 is rotated (clockwise is shown, but other directional designs are within the scope) to insert the latching pin 122 into the forward stopper slot 125, and the outer slider 119 was pulled away from handle section 115 and in the process slide the protective sleeve off the dilator 111 and retreats the protective sleeve 124 into the insertion tube 112.

Figure 11:
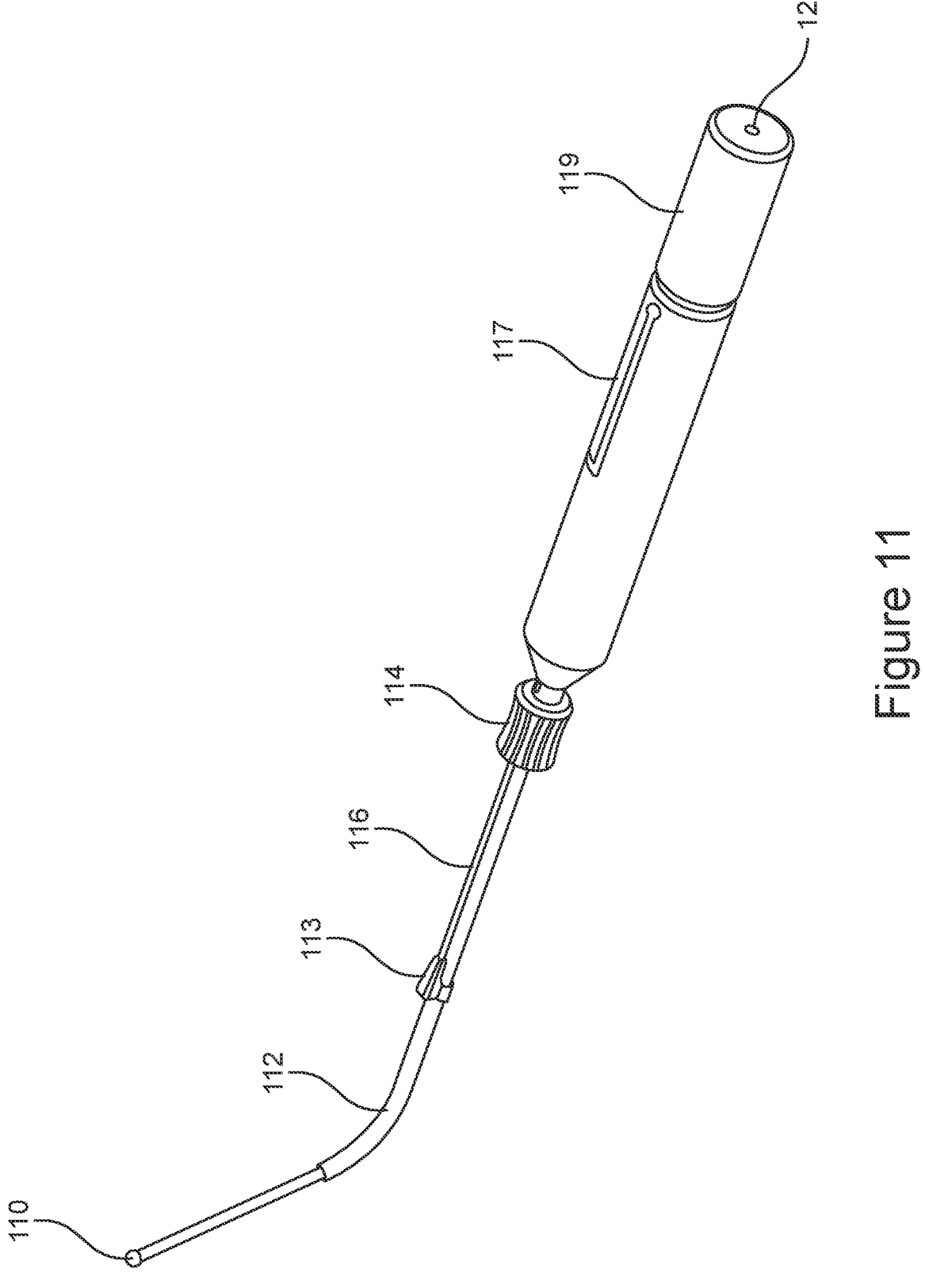
FIG. 11 is an illustration of an embodiment of the present invention.

When the procedure is completed, or the device needs to be withdrawn, the dilator 111 needs to be collapsed and covered again by the protective sleeve 124 to prevent tissue injury when sliding the device out from the eustachian tube treatment area. This is shown in FIG. 11 where there is shown the device with the outer slider 119 pushed inward again towards the handle section 115 so that the inner slider 118 slides fully inside the handle section 115. This moves and slides the protective sleeve 124 over the dilator 111 to and collapse and cover the dilator 111 inside the sleeve 124. Now that the protective sleeve buffers between the dilator 111 and the wall of the eustachian tube, the dilator 111 can be safely pulled out and removed from the eustachian tube without the risk of injury.

Figures 12, 13:
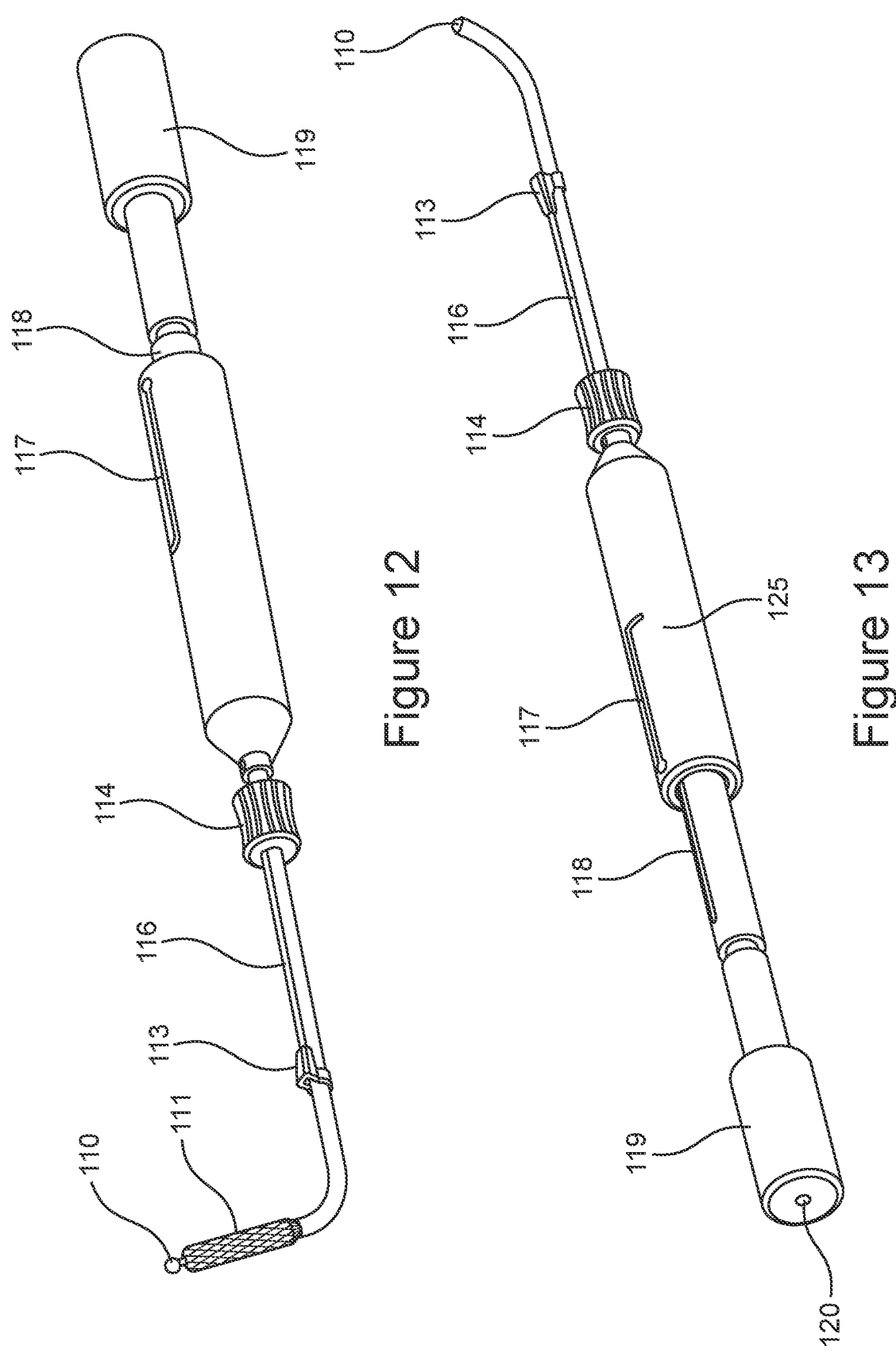
FIG. 12 is an illustration of an embodiment of the present invention.
FIG. 13 is an illustration of an embodiment of the present invention.

Referring to FIGS. 12 and 13, there are shown different perspectives of the delivery device of the present invention. In FIG. 12, the device is shown with the outer slider 119 partially extended and the protective sleeve 124 is withdrawn inside of insertion tube 112. The dilator 111 is exposed and expanded outside of the insertion tube 112. In FIG. 13, the device of the present invention is shown with the outer slider 119 and the inner slider 118 fully withdrawn from the handle section 115. The dilator 111 is withdrawn back inside of insertion tube 112 and within protective sleeve 124.

The devices and embodiments described herein may be made with materials identified herein or other materials known in the art and manufactured by processes known in the art as well for medical industry devices. It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A device for eustachian tube treatments comprising:
   a handle section having a proximal end and a distal end;
   said handle section having a dilator control as part of said handle section, said dilator control having at least a first position and a second position;
   said dilator control connected to a plate internal to said handle section; said plate connected to an internal shaft;
   a pin connected to said plate and contacting a latch;

an insertion tube connected and extending from said distal end of said handle section;

said insertion tube having an opening at a distal end of said insertion tube;

a protective sleeve inside of said insertion tube and connected at a first end of said protective sleeve to said plate;

a dilator connected at a first end of said dilator to said plate and collapsed within said protective sleeve, said dilator capable of expanding when moved to a position external to said distal end of said insertion tube and said protective sleeve is withdrawn back into said insertion tube.

2. The device according to claim 1 wherein said dilator control is moved to said second position to move said plate and said internal shaft forward and move said dilator and said protective sleeve to said position external to said distal end of said insertion tube.

3. The device according to claim 1 wherein said pin activates said latch.

4. The device according to claim 1 wherein said dilator comprises a mesh shape which expands when said protective sleeve is withdrawn.

5. The device according of claim 1 wherein said dilator forms a stent-like scaffold with open walls when expanded.

6. The device according to claim 1 wherein therapeutic treatment is delivered through said dilator.

7. The device according to claim 1 wherein said handle section has an opening at said proximal end that has a port.

8. The device according to claim 7 wherein said handle section includes a suction port.

9. The device according to claim 1 wherein said insertion tube is malleable.

10. The device according to claim 1 further comprising a camera control knob.

11. The device according to claim 10 further comprising a connecting tube connecting with and extending from said camera control knob to connect to a camera housing.

12. The device according to claim 11 wherein said camera housing includes a camera.

13. The device according to claim 1 wherein said dilator has an atraumatic distal section.

\* \* \* \* \*